US010463766B2

(12) United States Patent
Mentak

(10) Patent No.: US 10,463,766 B2
(45) Date of Patent: Nov. 5, 2019

(54) ULTRA VIOLET, VIOLET, AND BLUE LIGHT FILTERING POLYMERS FOR OPHTHALMIC APPLICATIONS

(75) Inventor: Khalid Mentak, San Ramon, CA (US)

(73) Assignee: KEY MEDICAL TECHNOLOGIES, INC., San Ramon, CA (US)

(*) Notice: Subject to any disclaimer, the term of this patent is extended or adjusted under 35 U.S.C. 154(b) by 215 days.

(21) Appl. No.: 12/954,985

(22) Filed: Nov. 29, 2010

(65) Prior Publication Data

US 2011/0071629 A1  Mar. 24, 2011

Related U.S. Application Data

(62) Division of application No. 11/350,396, filed on Feb. 8, 2006, now Pat. No. 7,842,367.

(60) Provisional application No. 60/677,917, filed on May 5, 2005.

(51) Int. Cl.

| | | |
|---|---|---|
| *A61L 27/16* | (2006.01) | |
| *C08F 222/10* | (2006.01) | |
| *A61L 27/50* | (2006.01) | |
| *G02B 1/04* | (2006.01) | |
| *G02C 7/10* | (2006.01) | |
| *A61F 2/16* | (2006.01) | |
| *C08F 212/32* | (2006.01) | |
| *C08F 226/12* | (2006.01) | |
| *C08F 220/26* | (2006.01) | |
| *C08F 220/18* | (2006.01) | |

(52) U.S. Cl.
CPC .............. *A61L 27/50* (2013.01); *A61F 2/16* (2013.01); *A61F 2/1659* (2013.01); *G02B 1/043* (2013.01); *G02C 7/104* (2013.01); *G02C 7/108* (2013.01); *A61F 2002/1699* (2015.04); *A61L 2430/16* (2013.01); *C08F 212/32* (2013.01); *C08F 220/18* (2013.01); *C08F 220/26* (2013.01); *C08F 222/1006* (2013.01); *C08F 226/12* (2013.01); *C08F 2220/1883* (2013.01); *Y10S 514/912* (2013.01); *Y10T 428/21* (2015.01); *Y10T 428/31935* (2015.04)

(58) Field of Classification Search
CPC ........ A61F 2/16; A61F 2/1659; A61F 2/1699; A61L 27/16; A61L 27/50; A61L 2430/16; G02B 1/043; C08F 212/32; C08F 220/18; C08F 220/26; C08F 2220/1883; C08F 222/1006; C08F 226/12; G02C 7/104; G02C 7/108; Y10T 428/21; Y10T 428/31935; Y10S 514/912
See application file for complete search history.

(56) References Cited

U.S. PATENT DOCUMENTS

| | | | |
|---|---|---|---|
| 4,304,895 A | 12/1981 | Loshaek | |
| 4,528,311 A | 7/1985 | Beard et al. | |
| 4,553,975 A * | 11/1985 | Su .......................... | D06P 3/008 351/159.33 |
| 4,856,889 A | 8/1989 | Guilino et al. | |
| 4,952,046 A | 8/1990 | Stephens et al. | |
| 5,026,395 A | 6/1991 | Nakajima et al. | |
| 5,269,813 A * | 12/1993 | Yoshida et al. .............. | 623/6.58 |
| 5,374,663 A | 12/1994 | Daicho et al. | |
| 5,400,175 A | 3/1995 | Johansen et al. | |
| 5,470,932 A | 11/1995 | Jinkerson | |
| 5,528,322 A | 6/1996 | Jinkerson | |
| 5,543,504 A | 8/1996 | Jinkerson | |
| 5,662,707 A | 9/1997 | Jinkerson | |
| 5,861,934 A | 1/1999 | Blum et al. | |
| 6,089,711 A | 7/2000 | Blankenbecler et al. | |
| 6,138,479 A | 10/2000 | Gille et al. | |
| 6,140,438 A * | 10/2000 | Ojio et al. ..................... | 526/264 |
| 6,281,319 B1 | 8/2001 | Mentak | |
| 6,329,485 B1 * | 12/2001 | Vanderbilt .............. | A61L 27/16 526/317.1 |
| RE38,402 E | 1/2004 | Stephens et al. | |
| 6,695,880 B1 | 2/2004 | Roffman et al. | |
| 7,446,157 B2 | 11/2008 | Mentak et al. | |
| 7,842,367 B2 | 11/2010 | Mentak | |
| 2002/0080451 A1 | 6/2002 | Hughes et al. | |
| 2004/0012757 A1 * | 1/2004 | Hong ............................. | 351/162 |
| 2005/0143812 A1 * | 6/2005 | Paul et al. ..................... | 623/6.3 |
| 2006/0004110 A1 | 1/2006 | Sabnis et al. | |
| 2006/0122349 A1 | 6/2006 | Mental et al. | |
| 2006/0252844 A1 | 11/2006 | Mentak | |

FOREIGN PATENT DOCUMENTS

| | | |
|---|---|---|
| CA | 1318755 | 6/1993 |
| CA | 2338245 A1 | 2/2000 |
| EP | 0488145 A2 | 6/1992 |
| JP | 01-299560 | 12/1989 |
| JP | 02-221914 | 4/1990 |

(Continued)

OTHER PUBLICATIONS

"Neue Orange Series Intraokularlinse von Ophtec" Ophta Jun. 2006 Sep. 1, 2005, pp. 56-57, XP008120393, Retrieved from the Internet:http://www.medilas.ch/Cms/UploadedDocuments/orange_series_ophtec.pdf(retrieved in Mar. 12, 2010.

(Continued)

*Primary Examiner* — John D Freeman

(74) *Attorney, Agent, or Firm* — Husch Blackwell LLP

(57) ABSTRACT

Opthalmic devices, particularly intraocular lenses (IOL), with improved contrast sensitivity and methods of making same. In one aspect, blue light blocking chromophores (BLBC) are diffused into, e.g. an IOL lens body to create a BLBC gradient in the lens. Orange dyes are preferred BLBCs.

9 Claims, No Drawings

(56) References Cited

FOREIGN PATENT DOCUMENTS

| JP | 03-118069 | 5/1991 |
|----|-----------|--------|
| JP | 03-144416 | 6/1991 |
| JP | 11-056999 | 3/1999 |
| JP | 11-0109296 | 4/1999 |
| JP | 03-144538 | 5/2003 |
| WO | WO9511279 | 4/1995 |
| WO | WO0034804 | 6/2000 |
| WO | 0173190 A1 | 10/2001 |

OTHER PUBLICATIONS

Supplementary European Search Report for EP 07763272 completed on Mar. 17, 2010.
Acrysof Natural single piece IOL, Product Monograph 2004 by Alcon Laboratories, Inc.
International Search Report for PCT App. No. PCT/US2007/061864 dated Jul. 10, 2007.
International Preliminary Report on Patentability for PCT App. No. PCT/US2007/061864 dated Aug. 12, 2008.
Non-Final Office Action for U.S. Appl. No. 11/350,396 dated Jun. 10, 2009.
Non-Final Office Action for U.S. Appl. No. 11/350,396 dated Dec. 8, 2009.
Final Office Action for U.S. Appl. No. 11/350,396 dated Jul. 21, 2009.

\* cited by examiner

ULTRA VIOLET, VIOLET, AND BLUE LIGHT FILTERING POLYMERS FOR OPHTHALMIC APPLICATIONS

CROSS-REFERENCE TO RELATED APPLICATIONS

This application is a divisional application of application Ser. No. 11/350,396 filed Feb. 8, 2006, now U.S. Pat. No. 7,842,367 issued Nov. 30, 2010, which is a non-provisional application of U.S. Provisional Application No. 60/677,917, filed May 5, 2005. The Ser. No. 11/350,396 application claims priority to U.S. Provisional Application No. 60/677,917 filed May 5, 2005 all of which are incorporated by reference in their entireties herein.

FIELD OF INVENTION

This invention relates to ophthalmic devices or apparatuses, particularly intraocular lenses (IOLS), with improved contrast sensitivity and protection from UV, violet, and blue light. This invention is particularly applicable to acrylic foldable IOLs and contact lenses. Novel methods of making ophthalmic devices also are disclosed.

BACKGROUND OF THE INVENTION

The assessment of optical hazards in recent years has led to the recognition of the possible hazards to the retina associated with blue light. Generally speaking blue light has a wavelength in the range of about 400-500 nm. If the blue light hazard is a real threat to vision, then the UV/visible transmission characteristics of ophthalmic lenses, and intraocular lenses (IOLs) in particular, should be modified to provide adequate protection from blue light hazards encountered in the environment.

In the ambient environment, solar radiation is the primary vision hazard. The sun freely emits UV, visible and IR radiation much of which is absorbed by the atmosphere. The solar radiation that is transmitted through the atmosphere and reaches the earth's surface consists of UV-B radiation (230-300 nm), near UV or UV-A radiation (300-400 nm), visible light (400-700 nm) and near IR radiation (700-1400 nm). The ocular media of man in its normal, healthy state freely transmits near IR and most of the visible spectrum to the retina. UV-B radiation is, however, absorbed by the cornea and does not reach the retina. UV-A and the blue portion of the visible spectrum can be absorbed by the crystalline lens of the eye depending upon the person's age.

The human crystalline lens changes its UV and visible transmission characteristics as it ages. In infancy the human lens will freely transmit near UV and visible light above 300 nm, but with further aging the action of UV radiation from the environment causes the production of yellow pigments, called fluorogens, within the lens. By approximately the age of 54 the lens will not significantly transmit light below 400 nm and the transmission of light between 400 and 500 nm is greatly diminished. As the lens ages it continuously develops a yellow color, increasing its capacity to filter out near UV violet, and blue light.

Currently, IOLs capable of blocking UV and blue light to varying degrees use yellow dyes. However, there are some major drawbacks with such IOLs:

1. Patients with yellow dye-containing IOLs experience reduced vision quality in dim light conditions. The yellow dyes used in current IOLs absorb light over of a relatively large band of wavelengths and a higher concentration is needed to achieve adequate blue light filtration. This causes a shift of absorption from the UV-violet-blue (200-420 nm) to the green region (420-470 nm).
2. The presence of blue light blocking chromophore in e.g., IOLs, reduces contrast sensitivity in some cases. Due to their intense yellow color (which the presence of blue light chromophores imparts to IOLs), blue light blocking chromophores in IOLs and other ophthalmic devices may interfere with color perception.

SUMMARY OF THE INVENTION

The present invention, in one aspect, is the use of a chromophore (dyes) or a combination of chromophores to optimize UV, violet, and blue light filtering of polymeric ophthalmic devices, particularly IOLs. It has been discovered that using one or more selected chromophores, with specific wavelength absorptions, and low concentrations, affords ophthalmic devices specifically including but not limited to, IOLs, more particularly described below, with improved light transmission characteristics.

Thus, in one embodiment, the present invention comprises an ophthalmic device, which includes polymerizable orange chromophores. Preferred polymerizable orange chromophores include but are not limited to: disperse orange 3 acrylamide, disperse orange 3 methacrylamide, disperse orange 3 acrylate, disperse orange 3 methacrylate, disperse orange 25 acrylamide, disperse orange 25 methacrylamide, disperse orange 25 acrylate, disperse orange 25 methacrylate, and 10-Dodecylacridine Orange Bromide.

Other orange chromophores include but are not limited to:
ACID ORANGE 12 (CROCEINE ORANGE C.I. 15970)
ACID ORANGE 128 (MERPACYL ORANGE R) (1)
ACID ORANGE 132 (MERPACYL YELLOW AR)
ACID ORANGE 19 (SUPRAMINE RED GGA)
ACID ORANGE 2 B (1)
ACID ORANGE 3 (C.I. 10385) (1)
ACID ORANGE 33 (C.I. 24780) (1)
ACID ORANGE 34 (CHROMACYL ORANGE GR) (1)
ACID ORANGE 43 (XYLENE FAST ORANGE P) (1)
ACID ORANGE 47 (BENZYL FAST ORANGE G) (1)
ACID ORANGE 5 (ACID YELLOW D C.I. 13080) (1)
ACID ORANGE 51 (1)
ACID ORANGE 60 (CAPRACYL ORANGE R) (1)
ACID ORANGE 62 (NEOLAN ORANGE GRE) (1)
ACID ORANGE 63
ACID ORANGE 63 (POLAR YELLOW R OR SUPRANOL YELLOW RA) (1)
ACID ORANGE 64 (CAPRACYL YELLOW 3 RD) (1)
ACID ORANGE 74 (1)
ACID ORANGE 74 (NEOLAN ORANGE G OR GYCOLAN ORANGE GL) (1)
ACID ORANGE 79 (C.I. 23255) (1)
ACID ORANGE 8 (1)
ACID ORANGE 86 (IRGALAN ORANGE RL) (1)
ACID ORANGE 87 (CIBALAN YELLOW 2 BRL) (1)
ACID ORANGE 94 (IRGANOL ORANGE GRLS) (1)
ACID ORANGE CAPRACYL BROWN HRN (1)
ACID ORANGE GG CRYSTALS (1)
ACRIDINE ORANGE 10-NONYL BROMIDE (2)
AMANIL FAST ORANGE ER (1)
AMIDINE FAST ORANGE 2 RL (1)
ANTHANOL CHROME ORANGE R (1)
ASTRAZON ORANGE G (1)
ASTRAZON ORANGE R (1)
AZOANTHRENE GOLDEN ORANGE R (1)

BASIC ORANGE 21 (GENACRYL ORANGE G) (1)
BASIC ORANGE 22 (GENACRYL ORANGE R) (1)
BASIC ORANGE 24 (SEVRON ORANGE L) (1)
BASIC ORANGE 25 (SEVRON ORANGE CL) (1)
BASIC ORANGE 26 (SEVRON BROWN YL) (1)
BASIC ORANGE 27 (ASTRAZON ORANGE 3 RL) (1)
BASIC ORANGE 28 (ASTRAZON ORANGE RRL) (1)
BASIC ORANGE 29 (ASTRAZON GOLDEN YELLOW GLD) (1)
BASIC ORANGE 30 (ASTRAZON YELLOW BROWN 2 GL) (1)
BASIC ORANGE 4-11 (C.I. 46035) (1)
BASIC ORANGE 43 (DEORLENE FAST ORANGE 2 GL) (1)
BASIC ORANGE 54 (MAXILON ORANGE 4 RL EXTRA CONC.) (1)
BENZANOL ORANGE R (1)
BENZO FAST ORANGE 2 RL (1)
BENZO FAST ORANGE WS (1)
BENZYL ORANGE (1)
BROMOCRESOL ORANGE (1)
BUFFALO DIRECT ORANGE Y (1)
C.I. 326 AMANIL FAST ORANGE S (1)
C.I. 621 AMANIL FAST ORANGE CG (1)
CALCO ACID ORANGE II (1)
CALCOCHROME ORANGE R EXTRA CONC. (1)
CALCOCID FAST LIGHT ORANGE 2 G (1)
CALCOCID MILLING ORANGE 4 R CONC. (1)
CALCOCID ORANGE Y EXTRA CONC. (1)
CALCODUR ORANGE EGL (1)
CALCODUR ORANGE GL (1)
CALCOFAST WOOL ORANGE 4 RN (1)
CALCOFORM ORANGE 5 RE (1)
CALCOLITE FAST ORANGE 3 R (1)
CALCOLOID FLAMING ORANGE 6 RD EXTRA CONC. (1)
CALCOLOID GOLDEN ORANGE 4 RD (1)
CALCOLOID GOLDEN ORANGE GD EXTRA CONC. (1)
CALCOLOID GOLDEN ORANGE RRTD EXTRA CONC. (1)
CALCOLOID ORANGE RD EXTRA CONC. (1)
CALCOMET ORANGE G (1)
CALCOMINE FAST ORANGE 2 RS EXTRA (1)
CALCOMINE FAST ORANGE E3G (1)
CALCOMINE FAST ORANGE EG (1)
CALCOMINE FAST ORANGE ER (1)
CALCOMINE ORANGE 2RS (1)
CALCOMINE ORANGE R SPECIAL (1)
CALCONESE BRILLIANT ORANGE GF CONC. (1)
CALCONESE ORANGE 3 RC (1)
CALCONESE ORANGE G (1)
CALCOSOL GOLDEN ORANGE RRTP (1)
CALCOSOL PRINTING ORANGE RY (1)
CALCOZINE ORANGE RS (1)
CALCOZINE ORANGE YC (1)
CAMACYL BRILLIANT ORANGE JER (1)
CAPRACYL ORANGE RP (1)
CELACYL BRILLIANT ORANGE 3 R (1)
-HYDROXY-1,4-NAPHTHOQUINONE (1)
CHRYSOIDINE G (2)
SUDAN II (1)
TROPAEOLIN 000 NO. 1 (1)
TROPAEOLIN O (1)
TROPAEOLIN O SODIUM SALT (1)
TROPAEOLIN OO (1)
THIOXINE ORANGE R (1)
TOLUYLENE FAST ORANGE LX (1)
VARINYL ORANGE DAC (1)
VAT ORANGE 1 (C.I. 59105) (1)
VAT ORANGE 24 (PONSOL GOLDEN ORANGE 3 GND EXTRA) (1)
VAT ORANGE 3 (C.I. 59300) (1)
VAT ORANGE 7 (SOLANTHRENE BRILLIANT ORANGE FJRA) (1)
VAT ORANGE 9 (C.I. 59700) (1)
VEGENTINE ORANGE CSW (1)
VERANTHRENE GOLDEN ORANGE 3 G (1)
SUDAN ORANGE G (2)
SULFONINE ORANGE GS CONC. (1)
SULPHUR ORANGE (1)
SUPERLITE FAST ORANGE RT (1)
SUPRAMINE ORANGE G (1)
SUPRANOL ORANGE RA (1)
TANNIN ORANGE (1)
TECTILON ORANGE 2 RT (1)
THIAZOLE ORANGE (2)
SOLVENT ORANGE 1 (NEWPORT OIL YELLOW C.I. 11920) (1)
SOLVENT ORANGE 20 (AZOSOL FAST ORANGE RA) (1)
SOLVENT ORANGE 23 (IOSOL ORANGE) (1)
SRA GOLDEN ORANGE FSI POWDER (1)
SRA GOLDEN ORANGE I POWDER (1)
SRA LIGHT ORANGE FSI (1)
SRA ORANGE BL (1)
SRA ORANGE I POWDER (1)
SRA ORANGE II POWDER
SODIUM 4-(3-(2,4-DI-ME-PH-AZO)-2,4-DI-HO-PH-AZO)-BENZENESULFONATE (ACID ORANGE 24 (1)
SODIUM 4-(4-(BENZYL-ET-AMINO)-PH-AZO)-2,5-DI-CL-BENZENESULFONATE (ACID ORANGE 50) (1)
SODIUM 5-(4-CL-PH-AZO)-6-HO-NAPHTHALENE-2-SULFONATE (ACID ORANGE 31 C.I. 15995) (1)
SOLOPHENYL ORANGE TGL (1)
REACTIVE ORANGE 5 (CIBACRON BRILLIANT ORANGE GP) (1)
REACTIVE ORANGE 68 (LANASOL ORANGE R) (1)
REACTIVE ORANGE 70 (CIBACRON GOLDEN YELLOW RE) (1)
REACTONE ORANGE G (1)
RESIST ORANGE N (1)
RESOLIN ORANGE 5 R (1)
RORACYL ORANGE R (1)
ROSANTHRENE ORANGE 3 R CONC. (1)
ROSANTHRENE ORANGE RSS (1)
SETACYL ORANGE P-RFL (1)
REACTIVE ORANGE 13 (PROCION ORANGE H-2R) (1)
REACTIVE ORANGE 16 (1)
REACTIVE ORANGE 2 (CIBACRON BRILLIANT ORANGE 2G-E) (1)
REACTIVE ORANGE 29 (LANASOL ORANGE G) (1)
REACTIVE ORANGE 35 (CIBACRON ORANGE 4 R-A) (1)
REACTIVE ORANGE 44 (CIBACRON PRONT ORANGE G) (1)
REACTIVE ORANGE 45 (CIBACRON PRONT GOLDEN YELLOW 2 R) (1)
REACTIVE ORANGE 46 (CIBACRON PRONT ORANGE BROWN 3 R) (1)
PONTAMINE FAST ORANGE 2 G CONC. (1)
PONTAMINE FAST ORANGE MR (1)
PONTAMINE FAST ORANGE MRL (1)
PONTAMINE FAST ORANGE RGL EXTRA CONC. (1)

PONTAMINE FAST ORANGE S (1)
PROCION ORANGE MX2R (1)
PROCION ORANGE MXG (1)
PYRAMINE ORANGE 3 G (1)
PYRAMINE ORANGE R (1)
PYRAZOL FAST ORANGE RL (1)
POLYDYE HISPERSE ORANGE 5 RH (1)
POLYFORM ORANGE RF EXTRA CONC. (1)
POLYPROPYLENE ORANGE Y (1)
PONSOL BRILLIANT ORANGE RKD EXTRA CONC. (1)
PONSOL GOLDEN ORANGE 4 RD EXTRA CONC. (1)
PONSOL GOLDEN ORANGE G EXTRA CONC. (1)
PONSOL GOLDEN ORANGE GD EXTRA CONC. (1)
PONSOL GOLDEN ORANGE RRTD EXTRA CONC. (1)
PONTACHROME ORANGE 4 G (1)
PONTACHROME ORANGE RL (1)
PARA BRILLIANT ORANGE G (1)
PARANOL FAST ORANGE EG (1)
PARANOL FAST ORANGE ER (1)
PARANOL FAST ORANGE GL (1)
POLAR ORANGE R CONC. (1)
POLY (DISPERSE ORANGE 3 ACRYLAMIDE) (1)
POLY (DISPERSE ORANGE 3 METHACRYLAMIDE) (1)
POLY[METHYL METHACRYLATE-CO-(DISPERSE ORANGE 3 ACRYLAMIDE)](1)
POLY[METHYL METHACRYLATE-CO-(DISPERSE ORANGE 3 METHACRYLAMIDE)](1)
ORANGE G (5)
ORANGE G SOLUTION (1)
ORANGE GG (1)
ORANGE GS (1)
MORDANT ORANGE 34 (CHROMAVEN BRILLIANT ORANGE 2 R) (1)
MORDANT ORANGE 8 (OMEGA CHROME ORANGE ML) (1)
NABOR ORANGE G (1)
NABOR ORANGE R (1)
NAPTHANIL ORANGE R BASE (1)
NATIONAL CHROMOLAN ORANGE R (1)
NATIONAL WOOL ORANGE A CONC. (1)
NATURAL YELLOW 8, 11 (ANRANTINE OSAGE ORANGE C.I. 75660) (1)
NEUTRACYL ORANGE R (1)
NEUTRAL ORANGE O (1)

Generally speaking, any polymerizable orange dye may be used in this embodiment of this invention. "Orange dye" for purposes of this invention includes polymerizable dyes having a coefficient of extinction "e" of at least 1500 $M^{-1} cm^{-1}$, preferably 3000 $M^{-1} cm^{-1}$, and most preferably 5000 $M^{-1} cm^{-1}$ for the region between 350 nanometers (nm) and 500 nm. Coefficients of distinction would, of course, be well known to one skilled in the art.

In a further embodiment, the present invention includes polymeric ophthalmic devices which comprise orange dyes or orange chromophores as set forth above and include an ethylenically unsaturated anthracene moiety e.g., vinyl anthracene.

In yet a further embodiment, the present invention comprises polymeric ophthalmic devices comprising orange chromophores or dyes as set forth above and substituted hydroxybenzophenones and substituted hydroxybenzotriazoles. Preferred benzophenones include the 2-hydroxybenzophenones disclosed in U.S. Pat. No. 4,304,895. While preferred benzotriazoles include the 2-hydroxy-5-acryloxyphenyl-2H-benzotriazoles disclosed in U.S. Pat. No. 4,528,311, both said patents being incorporated by reference herein. A most preferred ultraviolet-absorbing compound in this family is 2-3'-methallyl-2'-hydroxy-5' methyl phenyl benzotriazole.

In one variation of this invention, polymerizable orange dyes or chromophores are created or synthesized from non-polymerizable orange dyes by derivatizing the orange dye, e.g., to add a polymerization functionality. In one embodiment of this variation, a non-polymerizable orange dye is reacted with a selected species to add a site of ethylenic or vinylic unsaturation, i.e., double bond functionality. A suitable orange dye may be modified to add multiple reaction sites. Reaction sites, other than free-radically polymerizable sites, also may be added or created depending upon dye characteristics.

One skilled in the art will appreciate that the polymerizable orange dye is the resulting product of the derivatization reaction. Put otherwise, a polymerizable orange dye must be produced from the derivatization reaction but need not be an orange dye starting material, as defined herein. A dye could become both polymerizable and "orange" as described herein in a derivatization reaction were the right functionality added or chemical structure modification made e.g., dehydrogenation of a non-orange dye reactant, starting material. The syntheses described at paragraphs 20, 21, and 22, below illustrate this embodiment of the invention.

In yet a further embodiment, the present invention comprises polymeric ophthalmic devices including polymerizable orange chromophores or dyes set forth above and further comprises benzotriazoles, benzophenones, and ethylenically unsaturated anthracene moieties, as set forth above. In essence, a mixture of the classes of chromophores to which the present invention related may be used.

One skilled in the art will appreciate that while a present invention is primarily described in terms of IOLs, there are many ophthalmic devices whose characteristics will be enhanced by application of the teaching of the present disclosure.

DETAILED DESCRIPTION OF THE INVENTION

Ophthalmic Device Base Polymer

Suitable monomers for use in polymeric ophthalmic device of the present invention include but are not limited to carbazole and/or naphthyl moiety, carbazole, naphthalene, or a naphthyl group such as vinyl carbazole, vinyl naphthalene, lauryl methacrylate, stearyl methacrylate, methyl methacrylate, 2-hydroxyethyl acrylate, 2-hydroxyethyl methacrylate, 3-hydroxypropyl acrylate, 3-hydroxypropyl methacrylate, n-vinyl pyrrolidone, styrene, eugenol (4-hydroxyvinylbenzene), alpha.-methylstyrene. In addition, for high-refractive index foldable lens applications, suitable monomers include, but are not limited to: 2-ethylphenoxy methacrylate, 2-ethylphenoxy acrylate, 2-ethylthiophenyl methacrylate, 2-ethylthiophenylacrylate, 2-ethylaminophenyl methacrylate, phenyl methacrylate, benzyl methacrylate, 2-phenylethyl methacrylate, 3-phenylpropyl methacrylate, 4-phenylbutyl methacrylate, 4-methylphenyl methacrylate, 4-methylbenzyl methacrylate, 2-2-methylphenylethyl methacrylate, 2-3-methylphenylethyl methacrylate, 2-4-methylphenylethyl methacrylate, 2-(4-propylphenyl)ethyl methacrylate, 2-(4-(1-methylethyl)phenyl)ethyl methacrylate, 2-(4-methoxyphenyl)ethyl methacrylate, 2-(4-cyclohexylphenyl)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates. N-vinyl pyrolidone, styrene, eugenol and .alpha.-methyl styrene may also be suitable especially for high-refractive index foldable lens applications.

A preferred lens-forming monomer mixture is the mixture of vinyl carbazole, lauryl methacrylate, and hydroxyethyl acrylate. Conventional methods for polymerization of the preferred monomer mixture to a preferred polymeric lens material would be well known to one skilled in the polymer art.

A copolymerizable cross-linking agent is preferably used in the lens-materials of this invention such cross-linking may be any terminally or internally ethylenically unsaturated compound having more than one unsaturated group. Suitable cross-linking agents include, for example: ethylene glycol dimethacrylate, diethylene glycol dimethacrylate, allyl methacrylate, 1,3-propanediol dimethacrylate, allyl methacrylate, 1,6-hexanediol dimethacrylate, 1,4-butanediol dimethacrylate, and the like. A preferred cross-linking agent is ethylene glycol dimethacrylate. Suitable crosslinkers also include polymeric crosslinkers, such as, polyethylene glycol 1000 diacrylate, polyethylene glycol 1000 dimethacrylate, polyethylene glycol 600 dimethacrylate, polybutanediol 2000 dimethacrylate, polypropylene glycol 1000 diacrylate, polypropylene glycol 1000 dimethacrylate, polytetramethylene glycol 2000 dimethacrylate, and polytetramethylene glycol 2000 diacrylate.

Chromophore System

To achieve optimal light transmission and UV, violet, and blue light blocking, the chromophores described above may be used separately or in various combinations with concentrations varying from about 0.001% to 10% by weight comprises a mixture preferably about 0.002% to about 5% by weight, and most preferably about 0.003% to about 3% by weight. A preferred formulation contains one or more chromophores selected from each of the three classes of chromophores discussed above.

Synthesis of Polymerizable Orange Dyes
Disperse Orange 3 methacrylamide Synthesis 0.6 g of sodium hydride was added carefully to a 3 neck flask equipped with a condenser, addition funnel, and magnetic bar. 75 ml of anhydrous THF was added and the mixture stirred for 10 minutes. A solution of 4.0 g 4-(4-nitrophenylazo)aniline in 75 ml THF was added drop-wise and the flask stirred at 50° C. The temperature was raised to 95° C., and the mixture was refluxed for 6 hrs. The mixture was allowed to cool to room temperature and then 6.0 g of methacrylic acid in 20 ml THF was added drop-wise. The mixture was again refluxed for 8 hrs. The solution was cooled to room temperature. THF was evaporated to reveal a dark orange solid. The solid was washed thoroughly with dilute HCl and water. The product was recrystallized in 95% methanol. The yield was 56%.

Disperse Orange 25 Methacrylamide Synthesis

3-[N-Ethyl-4-(4nitrophenylazo)phenylamino]propionitrile was used instead of 4-(4-nitrophenylazo)aniline in the above procedure. The yield was 42%.

Disperse Orange 3 Acrylamide Synthesis 0.6 g of sodium hydride was added carefully to a 3 neck flask equipped with a condenser, addition funnel, and magnetic bar. 75 ml of methylene chloride was added and the mixture stirred for 10 minutes. A solution of 4.0 g 4-(4-nitrophenylazo)aniline in 75 ml methylene chloride was added drop-wise and the flask stirred at 50° C. The temperature was raised to 95° C., and the mixture was refluxed for 6 hrs. The mixture was allowed to cool to room temperature and then 6.0 g of acrylic acid in 20 ml methylene chloride was added drop-wise. The mixture was again refluxed for 8 hrs. The solution was cooled to room temperature. Methylene chloride was evaporated to reveal a dark orange solid. The solid was washed thoroughly with dilute HCl and water. The product was recrystallized in 95% methanol. The yield was 35%.

Disperse Orange 25 Acrylamide Synthesis

3-[N-Ethyl-4-(4nitrophenylazo)phenylamino]propionitrile was used instead of 4-(4-nitrophenylazo)aniline in the above procedure. The yield was 38%.

Commercially available chromophores may in some instances be used. Care must be taken to remove any residual initiators, processing aids or other extraneous additives, including unpolymerized monomer(s), which might not be suitable for long-term exposure to ophthalmic fluid or to the ophthalmic environment.

Methods of Manufacture
General Preparation Steps for Polymers of Example 1-10

The comonomers listed below were mixed in a glass flask using a magnetic stir bar for at least 30 minutes followed by sonication for 30 minutes at a power setting of 100% on a Branson 5510 and then stirring again for another 30 minutes. The combination of sonication and hydrophilic/hydrophobic repulsion forces allows the formation of nanoclusters. AIBN was added at a concentration of 0.2% by weight. The comonomer mixture was vacuum degassed and placed in a Teflon tubular mold. The mold was placed in water bath at 70° C. for 12 hours than cured at 100° C. for 12 hours. A polymer rod measuring 19 mm in diameter and 6 inches in length was removed from the mold, cured for 12 hours at 100° C. and annealed for 14 hours at 100° C. for further processing. The polymer rod was machined into 17 mm×2 mm disks and IOLs were cut from the samples.

The refractive index was measured using a CLR 12-70 refractometer from Index Instrument. The optical properties of the IOLs were measured by UV/VIS spectroscopy using a DU-50 spectrophotometer from Beckman Instruments. To assess the efficiency of UV light and blue light blocking, percent light transmittance was measured at key wavelengths including 400, 420, and 470 nm. A comparative analysis with a commercially available IOL containing a yellow dye (Acrysof Natural®) was included in the studies.

Examples 1-10

|   | Monomer | Conc. | RI | % Transmittance | | |
|---|---------|-------|-----|------|------|------|
|   |         |       |     | 400 nm | 420 nm | 470 nm |
| 1. | VC | 30 | 1.569 | 10 | 23 | 53 |
|   | LM | 37 | | | | |
|   | HEMA | 29.5 | | | | |
|   | EGDM | 2.92 | | | | |
|   | DOM2 | 0.08 | | | | |
|   | 5 VA | 0.5 | | | | |
| 2. | VC | 30 | 1.568 | 14 | 27 | 65 |
|   | LM | 36.7 | | | | |
|   | HEA | 30 | | | | |
|   | EGDM | 2.92 | | | | |
|   | DOA3 | 0.08 | | | | |
|   | MEB | 0.3 | | | | |

-continued

|  | Monomer | Conc. | RI | % Transmittance | | |
|---|---|---|---|---|---|---|
|  |  |  |  | 400 nm | 420 nm | 470 nm |
| 3. | VC | 30 | 1.563 | 4 | 15 | 54 |
|  | EHA | 36.2 |  |  |  |  |
|  | HEMA | 30 |  |  |  |  |
|  | EGDM | 2.95 |  |  |  |  |
|  | DOM25 | 0.05 |  |  |  |  |
|  | VA | 0.5 |  |  |  |  |
|  | MEB | 0.3 |  |  |  |  |
| 4. | VC | 30 | 1.562 | 8 | 19 | 65 |
|  | EHA | 36.1 |  |  |  |  |
|  | HEA | 30 |  |  |  |  |
|  | EGDM | 2.95 |  |  |  |  |
|  | DOM3 | 0.05 |  |  |  |  |
|  | VA | 0.6 |  |  |  |  |
|  | MEB | 0.3 |  |  |  |  |
| 5. | VN | 30 | 1.554 | 7 | 9 | 54 |
|  | EHA | 36.3 |  |  |  |  |
|  | HEMA | 30 |  |  |  |  |
|  | EGDM | 2.95 |  |  |  |  |
|  | DOM25 | 0.05 |  |  |  |  |
|  | VA | 0.4 |  |  |  |  |
|  | MEB | 0.3 |  |  |  |  |
| 6. | VC | 29 | 1.551 | 1 | 2 | 48 |
|  | EHA | 37 |  |  |  |  |
|  | HEA | 30 |  |  |  |  |
|  | EGDM | 2.98 |  |  |  |  |
|  | DOA3 | 0.02 |  |  |  |  |
|  | VA | 1.0 |  |  |  |  |

PREFERRED FORMULATIONS

|  | Monomer | Conc. | RI | 400 nm | 420 nm | 470 nm |
|---|---|---|---|---|---|---|
| 7. | VC | 21.3 | 1.539 | 1 | 19 | 62 |
|  | HEA | 28.0 |  |  |  |  |
|  | LM | 46.7 |  |  |  |  |
|  | EGDM | 2.985 |  |  |  |  |
|  | DOM3 | 0.015 |  |  |  |  |
|  | VA | 0.7 |  |  |  |  |
|  | MEB | 0.3 |  |  |  |  |
| 8. | VC | 21.3 | 1.536 | 1 | 15 | 60 |
|  | HEA | 28.0 |  |  |  |  |
|  | LM | 46.7 |  |  |  |  |
|  | EGDM | 2.982 |  |  |  |  |
|  | DOM3 | 0.018 |  |  |  |  |
|  | VA | 0.7 |  |  |  |  |
|  | MEB | 0.3 |  |  |  |  |
| 9. | VC | 21.3 | 1.535 | 1 | 14 | 50 |
|  | HEA | 28.0 |  |  |  |  |
|  | LM | 46.7 |  |  |  |  |
|  | EGDM | 2.97 |  |  |  |  |
|  | DOM3 | 0.03 |  |  |  |  |
|  | VA | 0.7 |  |  |  |  |
|  | MEB | 0.3 |  |  |  |  |
| 10. | VC | 21.3 | 1.537 | 1 | 19 | 55 |
|  | HEA | 28.0 |  |  |  |  |
|  | LM | 46.7 |  |  |  |  |
|  | EGDM | 2.98 |  |  |  |  |
|  | DOM3 | 0.02 |  |  |  |  |
|  | VA | 0.7 |  |  |  |  |
|  | MEB | 0.3 |  |  |  |  |
| Acrysof Natural ® | not known |  |  | 6 | 28 | 57 |

VC: vinyl carbazole
VN: 2-vinyl naphthalene
EHA: 2-ethylhexylacrylate
LM: Lauryl methacrylate
HEMA: Hydroxyethylmethacrylate
HEA: Hydroxyethylacrylate
EGDM: ethylene glycol dimethacrylate
VA: vinyl anthracene
MEB: 2-(2'-Methacryloxy-5'methylphenyl)benzotriazole
DOM3: Disperse Orange 3 Methacrylamide
DOA3: Disperse Orange 3 Acrylamide
DOM25: Disperse Orange 25 Methacrylamide The results show that the novel chromophore system provides excellent UV, violet, and blue light filtering without compromising light transmission at higher wavelengths.

The invention claimed is:

1. A foldable intraocular lens comprising:
   a copolymer of vinyl carbazole, 2-ethylhexylacrylate, ethylene glycol dimethacrylate, and vinyl anthracene,
   the lens further comprising a substituted hydroxy benzotriazole moiety or a substituted hydroxy benzophenone moiety; and an orange dye wherein the orange dye is selected from the group consisting of:
   disperse orange 3 acrylamide, disperse orange 3 methacrylamide, disperse orange 3 acrylate, disperse orange 3 methacrylate, disperse orange 25 acrylamide, disperse orange 25 methacrylamide, disperse orange 25 acrylate, disperse orange 25 methacrylate, and 10-dodecylacridine orange bromide,
   wherein the orange dye is present in a concentration in the range of about 0.001% to 10% by weight, and further wherein the orange dye has a coefficient of extinction ("e") of at least 1500 $M^{-1}$ $cm^{-1}$ for a region between 350 nanometers and 500 nm.

2. The foldable intraocular lens according to claim 1 wherein the orange dye is present in the range of about 0.002% to about 5% by weight.

3. The foldable intraocular lens according to claim 1 wherein the orange dye is present in the range of about 0.003% to about 3% by weight.

4. The foldable intraocular lens according to claim 1 further comprising hydroxyethylmethacrylate.

5. The foldable intraocular lens according to claim 1 further comprising hydroxyethylacrylate.

6. The foldable intraocular lens according to claim 1 wherein the substituted hydroxy benzotriazole moiety is 2-(2'-methacryloxy-5'-methylphenyl)benzotriazole.

7. The foldable intraocular lens according to claim 6, wherein the orange dye is disperse orange 25 methacrylamide.

8. The foldable intraocular lens according to claim 6, wherein the orange dye is disperse orange 3 acrylamide.

9. The foldable intraocular lens according to claim 6, wherein the orange dye is disperse orange 3 methacrylamide.

* * * * *